United States Patent [19]
Post

[11] Patent Number: 5,728,139
[45] Date of Patent: Mar. 17, 1998

[54] AUTOMATIC WAVEFORM SELECTION FOR DEFIBRILLATION

[75] Inventor: William L. Post, McMinnville, Oreg.

[73] Assignee: Hewlett-Packard Company, Palo Alto, Calif.

[21] Appl. No.: 741,891

[22] Filed: Oct. 31, 1996

[51] Int. Cl.$^6$ ............................................. A61N 1/39
[52] U.S. Cl. .............................................. 607/6
[58] Field of Search ............................ 607/5, 6, 7, 8

[56] References Cited

U.S. PATENT DOCUMENTS

| | | |
|---|---|---|
| 4,637,397 | 1/1987 | Jones . |
| 4,869,252 | 9/1989 | Gilli . |
| 4,932,407 | 6/1990 | Williams . |
| 4,998,531 | 3/1991 | Bocchi et al. . |
| 5,014,696 | 5/1991 | Mehra . |
| 5,184,616 | 2/1993 | Weiss . |
| 5,184,620 | 2/1993 | Cudahy et al. . |
| 5,352,239 | 10/1994 | Pless . |
| 5,366,485 | 11/1994 | Kroll et al. . |

*Primary Examiner*—Scott M. Getzow

[57] ABSTRACT

A method and device for efficient defibrillation, to be utilized in external defibrillation machines, capable of being utilized with 2, 3, or more defibrillation electrodes. The method and device achieve the efficient defibrillation by ensuring that the defibrillation machine energizes the patient with the waveform which is optimum for the number of defibrillation electrodes in use. The method and device accomplishes this by (1) sensing the number of defibrillation electrodes in use, and by (2) selecting the optimum defibrillation waveform for energization of the sensed number of defibrillation electrodes in use.

6 Claims, 3 Drawing Sheets

AUTOMATIC WAVEFORM SELECTION FOR DEFIBRILLATION

BACKGROUND OF THE INVENTION

1. Technical Field

The present invention relates, in general, to an improved external defibrillator and, in particular, to an improved external defibrillator having automatic waveform selection. Still more particularly, it relates to an improved external defibrillator having automatic waveform selection by sensing the number of electrodes in use.

2. Description of the Related Art

The heart is generally described as being composed of four chambers: the right atrium, the right ventricle, the left atrium, and the left ventricle. There is a one-way valve between the right atrium and the right ventricle (the tricuspid valve). There is a one-way valve between the right ventricle and the arterial system which perfuses the lungs (the pulmonary valve). There is a one-way valve between the left atrium and the left ventricle (the mitral valve). And, lastly, there is a one-way valve between the left ventricle and the aorta (the aortic valve).

In terms of its functional operation, the heart receives oxygen-depleted blood via the vena cavae (the two large veins which return blood to the heart). These large veins empty into the right atrium. The right atrium then pushes this oxygen-depleted blood into the right ventricle. Next, the right ventricle pushes this oxygen-depleted blood into one long, continuous fluid path composed of, in sequence, the pulmonary artery, the capillary beds perfusing the lungs, and the pulmonary veins which empty into the left atrium; the continuous path ends with the left atrium, which is to say that there is no valve between the pulmonary veins and left atrium. Next, the oxygen rich blood which has entered the left atrium is pushed into the left ventricle. Finally, the left ventricle pushes the blood out into the aorta.

The heart pumps blood by the organized successive contraction of individual heart muscle fibers. A neurological signal spreads through the heart, and each muscle fiber responds by contracting in sequence. The overall effect is a single heartbeat, or heart pulse, moving blood through the heart. For effective pumping, the muscle fibers must contract in an organized fashion.

The neurological signal alluded to in the previous paragraph is effectuated by the spread of an action potential throughout the heart. An action potential is a transient change in cell membrane potential which conveys information, such as the information in a signal telling a heart muscle fiber to contract. When the heart muscle is at rest, the electrical potential on either side of any cell membrane is maintained at a fixed potential. However, when the muscle is stimulated, either electrically, chemically, or mechanically, channels open in the membrane which allow the oppositely charged ions on either side of the membrane to cross the membrane, such ions engaging in an effort to reach electrical and thermal neutrality. This occurrence is referred to as "depolarization," since the system is becoming less polarized as the ions tend toward the lowest energy state. If the stimulation is great enough, the change in potential arising from the ions crossing the membrane will be great enough to depolarize the portion of the membrane directly adjacent to the area of the membrane depolarized by the stimulus. When this occurs, an action potential is said to have been initiated, and the signal will continue to propagate through the fiber via the just-described mechanism of depolarizing that portion of the membrane directly adjacent to the depolarized area. This propagation of the action potential is analogous to the way in which a row of dominoes falls when the first is flicked into the second, and the second falls into the third, and the third falls into the fourth, etc. Once the action potential has propagated past a region of the membrane, the cell membrane resets itself in a process known as "repolarization." In repolarization, ions are actively pumped back across the cell membrane to restore the polarized state.

The functional operation, described above, is effectuated by the electrochemical and mechanical operation of the heart as follows. The natural pacemaker of the heart, the sinoatrial nerve, discharges an electrochemical pulse, or action potential, and from this action potential all subsequent electrochemical and mechanical activity of the heart ensues. The sinoatrial nerve is located very near the right atrium, so the initial action potential reaches it almost immediately; simultaneously, the action potential propagates along a very fast conduction internodal tract to the left atrium, with the net result being that the atria (plural of atrium) receive the pulse almost simultaneously. Due to the anatomical structure of the heart, the atria initially receive the pulse upstream from the atrioventricular valves which separate the atria from the ventricles. When the pulse is received, the muscle fibers excited first contract first; in practice, what this means is that the atria of the region upstream contract first, so that the blood is pushed in the downstream direction. This operation is greatly analogous to the way in which toothpaste can be most efficiently squeezed out of the tube by squeezing at the closed end of the tube first.

Although, at this point, the atria have received the action potential, it (the action potential) is continuing to propagate throughout the heart. Simultaneous with the just-described actions involving the atria, the action potential is proceeding over three parallel internodal tracts to the atrioventricular node. The atrioventricular node functions as an analog delay; this delay provides time for atrial contraction to occur (the atria contract with more force over time as more fibers are recruited into contraction), which will enhance the functioning of the atria. After the delayed action potential leaves the atrioventricular nerve, it is conducted along a neural structure known as the bundle of His. Subsequent to this, the neural structure splits and the action potential is conducted by the right and left bundle branches to the regions of the right and left ventricles. Once the action potential arrives at the regions of the right and left ventricles, the action potential activates the Purkinje fibers, which are very fast conduction fibers that conduct the action potential very rapidly over and throughout the ventricles.

Once the ventricles are energized (depolarized), they begin to contract. The ventricles are much stronger and contract more rapidly than the atria (which are, at this point, continuing to contract). Very quickly, the pressure in the ventricular chambers outstrips that of the atria, causing both the mitral and the tricuspid valves to slam shut (because the pressure on the upstream side of these one-way valves exceeds the pressure on the downstream side). Once the right ventricle has outstripped the pressure of the contracting left atrium, the pulmonary valve opens and blood is pumped into the fluid path consisting of the pulmonary artery, capillary bed, pulmonary vein, and left atrium. Subsequent to this, once the left ventricle has outstripped the pressure of the aorta, the aortic valve opens and blood is pushed into the aorta. Once the ventricles have ejected the majority of their contents, the ventricles begin to relax and both the pulmonary and aortic valves close, with the pulmonary valve generally closing first due to the proximity of the continuing-to-contract left atrium.

Once the pressure in the relaxing ventricles falls below that of the continuing-to-contract atria, the atrioventricular valves (tricuspid and mitral) open and the atria push blood into the ventricles. Once the atria have completed this task, they relax and the heart enters a wait state after which the whole foregoing-described process is re-initiated by the next sinoatrial pulse.

As has been alluded to above, it is very important that the action potential proceed as an orderly wave throughout the heart so that the heart muscles squeeze the blood through the lungs and out of the heart through the aorta and the rest of the body. That is, even the very rapid Purkinje fibers conduct the signal from first stimulated to last stimulated, which ensures the correct direction of "push." Returning to our toothpaste analogy, the orderly conduction of the wave assures that the tube will be squeezed from the correct end.

Imagine what would happen, then, if the beautifully synchronized action potential wave became disrupted. In fact, specifically imagine what would happen if the wave through the Purkinje fibers became unsynchronized such that a region of the fibers that was to be depolarized subsequent in time to another region further upstream spontaneously depolarized either before, or simultaneous with, the region that should have depolarized first. Note that the effect of this spontaneous depolarization would be the heart working against itself, in that if the regions simultaneously depolarized the blood would be simultaneously pushed forwards (upstream) and backwards (downstream) and would go nowhere; furthermore, if the regions sequentially depolarized but in the wrong order, the blood would be first pushed backwards and then forwards with the net result being that the blood would go nowhere. When this phenomenon occurs on a large scale, the result is termed "fibrillation."

A fibril is one of the fine threads into which a striated muscle can be longitudinally split. "Fibrillation" is a term coined in the mid-to-late 1800s and refers to the preceding-described unsynchronization to the point such that it appears each muscle fiber of the heart is contracting randomly and independent of the other fibers. Since the muscle fibers where the spontaneous action potentials occur contract, and since this contraction is not in any way synchronized with the other action potentials, the result is chaotic, with the result being that no blood is pumped out of the heart because the different parts of the heart muscle are not acting in synchrony. In fact, a heart in fibrillation is often described as resembling a quivering bag filled with worms, since the asynchronous contractions of different bands or fibers of muscle resembles the surface of a bag filled with writhing worms.

"Defibrillation" is the causing of the cessation of the chaotic and uncoordinated contraction of the ventricular myocardium arising from the spontaneously occurring action potentials by the application of an electrical voltage and current. Defibrillation is achieved when the electrical energy supplied is large enough to depolarize a major portion of the heart muscle such that virtually the entire heart muscle is simultaneously depolarized. Once this is done, all portions of the heart muscle repolarize virtually simultaneously and the heart is in its resting state. An analogous way to think of defibrillation is the resetting of the heart to its wait state. Then, once the sinoatrial nerve fires, the heart muscle propagates the action potential in the correct synchronous fashion, since the defibrillation put all portions of the heart back in synch.

In practice, it is sometimes difficult to electrically energize the heart such that the desired uniform depolarization occurs; furthermore, the stimulating signal must be of a type to avoid the possibility of itself reinducing fibrillation once it is terminated. Toward this end, physiologists have tried using various different stimulating waveforms in conjunction with various different numbers of stimulating defibrillation electrodes.

Experimentation has shown that there are optimal electrical waveforms to be utilized with various different numbers of defibrillation electrodes. That is, there is an optimum waveform to be utilized with two defibrillation electrodes, three defibrillation electrodes, four defibrillation electrodes, etc.

Unfortunately, although the need for waveforms which are optimized for use with different numbers of defibrillation electrodes is known, the prior art has not taken full advantage of this knowledge. That is, current external defibrillators use the same waveform irrespective of whether two, three, or four defibrillation electrodes are in use. Thus, it is apparent that there is a need for an external defibrillator which selects the optimum waveform based upon the number of defibrillation electrodes in use.

This need has not been addressed in the prior art. Most of the activity in the defibrillation field in recent years has been in the area of implantable defibrillators. As will be shown, in the prior art, devices exist which will detect the biological impedance between defibrillation electrodes and select the optimum waveform to be used based upon such sensing; however, none of these devices selects the waveform based upon the number of defibrillation electrodes actually connected to the defibrillator.

Weiss (U.S. Pat. No. 5,184,616) discloses an apparatus for generation of various waveforms in a defibrillator, and includes means to vary the energy waveforms delivered to the defibrillation electrodes based on the needs of the patient and the programming of the pacemaker/defibrillator. At col. 16, line 45, and col. 17, line 28, this patent appears to describe selection of waveforms based on "impedance" changes in the patient. This device does not select waveforms dependent upon the number of defibrillation electrodes in use.

Mehra (U.S. Pat. No. 5,014,696) discloses an endocardial defibrillation electrode system which includes the use of a variety of defibrillation pulse regimes that are optimized for use with the defibrillation electrode system. This device does not disclose or suggest the selection of waveforms dependent upon the number of defibrillation electrodes in use.

Cudahy et al. (U.S. Pat. No. 5,184,620) disclose a method of using a multiple electrode pad assembly, which includes measuring voltage differences between electrode sites and connecting electrodes for both defibrillation and return path with appropriate energy to the electrodes. This device does not disclose or suggest the selection of waveforms dependent upon the number of defibrillation electrodes in use.

In view of the foregoing, it should be apparent that a need exists for an improved method and device for use in external defibrillators, which senses the number of defibrillator electrodes in use and selects a waveform optimized for use with the number of defibrillation electrodes sensed.

SUMMARY OF THE INVENTION

It is therefore one object of the present invention to provide an improved external defibrillator.

It is another object of the present invention to provide an improved external defibrillator having automatic waveform selection.

It is yet another object of the present invention to provide an improved external defibrillator having automatic waveform selection by sensing the number of electrodes in use.

The foregoing objects are achieved as is now described. A method and device are provided for efficient defibrillation, to be utilized in external defibrillation machines, capable of being utilized with 2, 3, or more defibrillation electrodes. The method and device achieve the efficient defibrillation by ensuring that the defibrillation machine energizes the patient with the waveform which is optimum for the number of defibrillation electrodes in use. The method and device accomplish this by (1) sensing the number of defibrillation electrodes in use, and by (2) selecting the optimum defibrillation waveform for energization of the sensed number of defibrillation electrodes in use.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF PREFERRED EMBODIMENT

Figure 1:
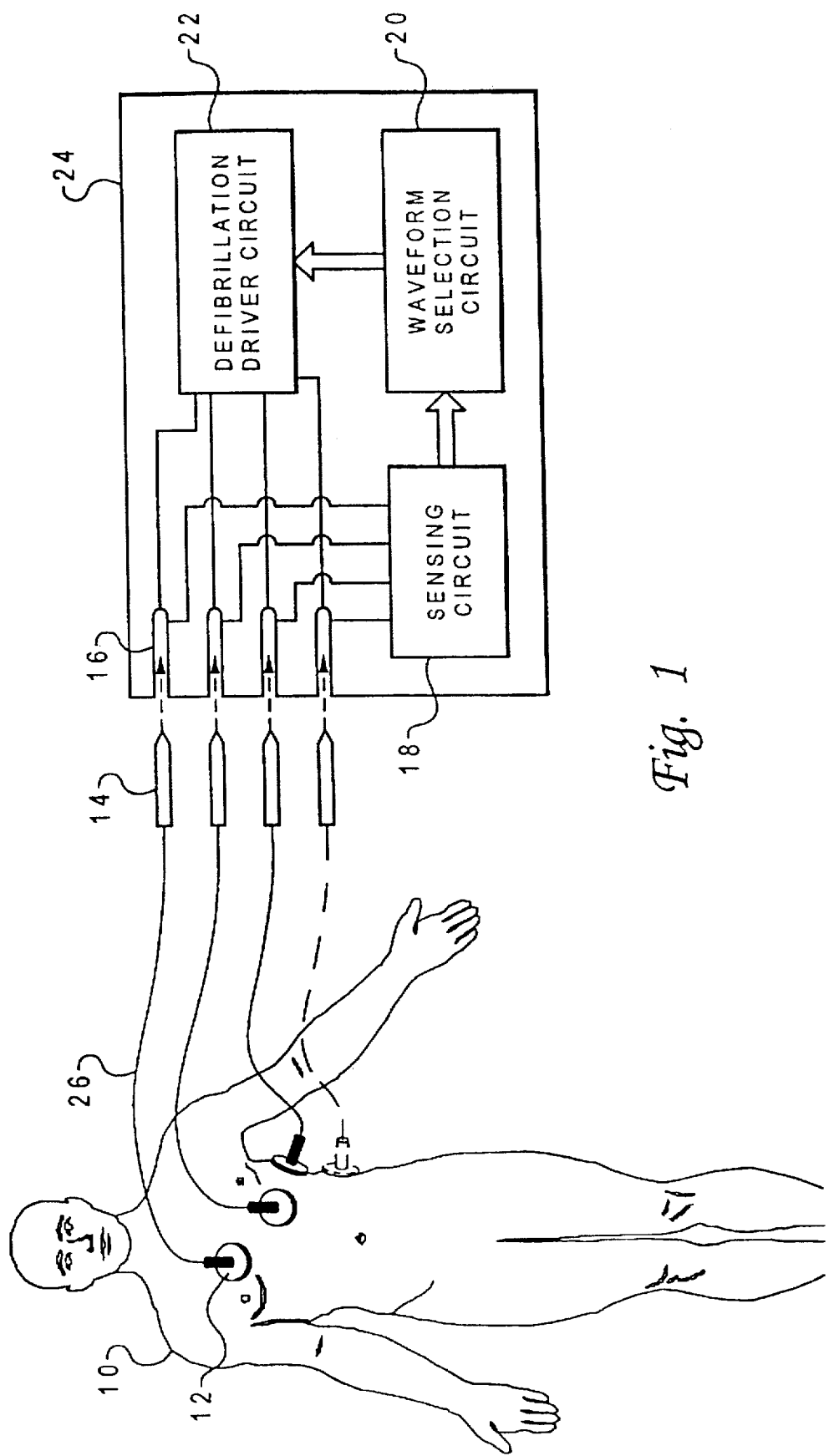
FIG. 1 illustrates a high-level schematic view of a system for implementing the present invention.

With reference now to the figures and in particular with reference to FIG. 1, there is depicted a high-level schematic view of a system for implementing the present invention. FIG. 1 depicts a person 10 to whom a number of defibrillation electrodes 12 are attached. In practice, the defibrillation electrodes would typically be held in place by one or more human operators, but in FIG. 1, the human operator(s) are not shown. The electrodes are connected by conducting cables 26 to connectors 14. The connectors 14 connect the defibrillation electrodes 12 via the conducting cables 26 to the defibrillation machine 24, by connecting with the electrode terminals 16. The sensing circuit 18 senses whether or not the connectors 14 have been placed into the electrode terminal 16. The sensing circuit 18 passes this information to the waveform selection circuit 20. The waveform selection circuit 20 takes the information from the sensing circuit 18 regarding the number of defibrillation electrodes 12 in use (a connector 14 in an electrode terminal 16 indicates that the associated defibrillation electrode 12 is in use) and consults its stored memory to find the optimal waveform to be used with the number of defibrillation electrodes 12 sensed by the sensing circuit 18 to be in use. The waveform selection circuit 20 passes this information to the defibrillation driver circuit 22 which uses this information to drive the defibrillation electrodes 12 with the appropriate optimized waveform.

Figure 2:
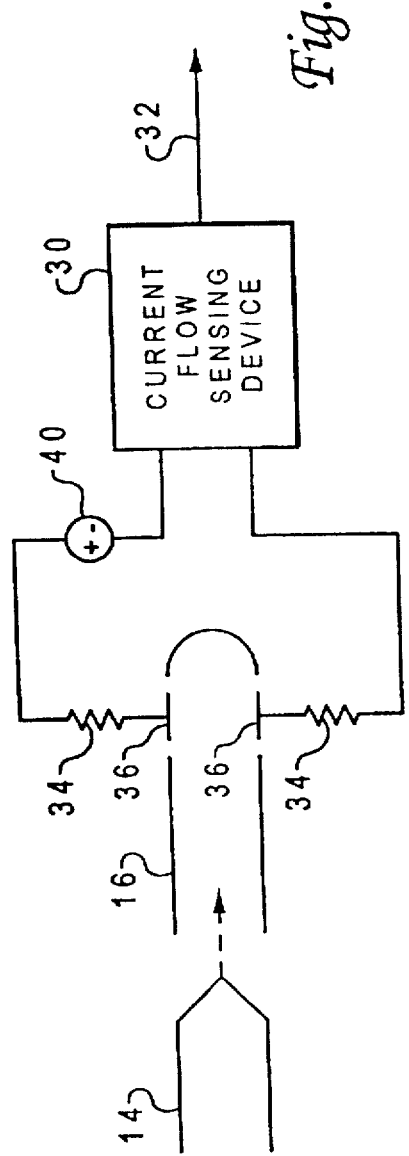
FIG. 2 is a schematic diagram illustrating a first embodiment of the sensing circuit 18 shown in FIG. 1.

Referring now to FIG. 2, which is a schematic diagram illustrating a first embodiment of the sensing circuit 18 shown in FIG. 1, note that if the connector 14 is inserted into the electrode terminal 16, the connector 14 will eventually interface with the electrical contacts 36 and thus provide a path for conduction between the electrical contacts 36. Once this conduction path has been established, the current from voltage source 40 will flow through the resistors 34, with the resistance of the resistors 34 being very large, meaning that these resistors are many orders of magnitude higher than any resistance that might be encountered in the circuit formed between any two defibrillation electrodes 12, separated by the person 10. Once this current begins to flow, the current flow sensing device 30 outputs a signal on its output line 32, which indicates a closed circuit condition exists. The closed circuit condition indicating that the defibrillation electrode 12 corresponding to the electrode terminal reference 16, to which the current flow sensing device 30 is connected, is in use.

Figure 3:
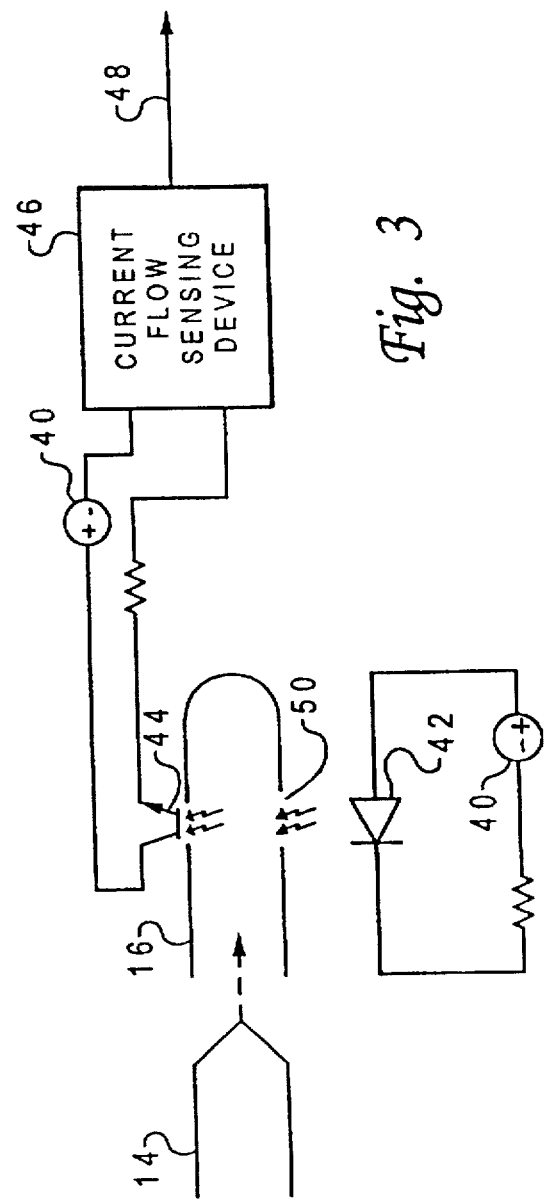
FIG. 3 is a schematic diagram depicting a second embodiment of the sensing circuit 18 shown in FIG. 1.

With reference now to FIG. 3, which is a schematic diagram depicting a second embodiment of the sensing circuit shown in FIG. 1, note that voltage source 40 drives a light-emitting diode 42. The electrode terminal 16 has a pathway 50 through which the light emitted by the light-emitting diode 42 may pass. Directly across from the light-emitting diode 42 through the pathway 50 through which the light emitted by the light-emitting diode 42 may pass is a photodiode 44. So long as the photodiode 44 is illuminated, the current from voltage source 40 is free to flow, and the current flow sensing device 46 senses a closed circuit condition. However, when the connector 14 is inserted into the electrode terminal 16, the pathway through the electrode terminal 16 is blocked, and the photodiode 44, no longer receiving any light, turns off. The current flow sensing device 46 no longer senses current and outputs on its output line 48 a signal indicating an open circuit condition exists. The open circuit condition indicating that the defibrillation electrode 12 corresponding to the electrode terminal reference 16, to which the current flow sensing device 46 is connected, is in use.

In FIG. 2, the presence of the connector 14 in the electrode terminal 16 is indicated by a closed circuit condition. In FIG. 3, the presence of the connector 14 in the electrode terminal 16 is indicated by an open circuit condition. As has been stated, these figures represent two different possible embodiments of the sensing circuit 18 in FIG. 1. Thus, depending upon the embodiment used, the waveform selection circuit 20 would be constructed so as to respond appropriately to either an open circuit or closed circuit condition; that is, if the waveform selection circuit 20 were being used with the embodiment shown in FIG. 2, the waveform selection circuit would recognize a closed circuit condition as indicating that the defibrillation electrode 12 corresponding to the electrode terminal 16 was in use. Whereas, if the embodiment depicted in FIG. 3 were used, then the waveform selection circuit 20 would recognize an open circuit condition as an indication that the defibrillation electrodes 12 corresponding to electrode terminal 16 was in use.

Figure 4:
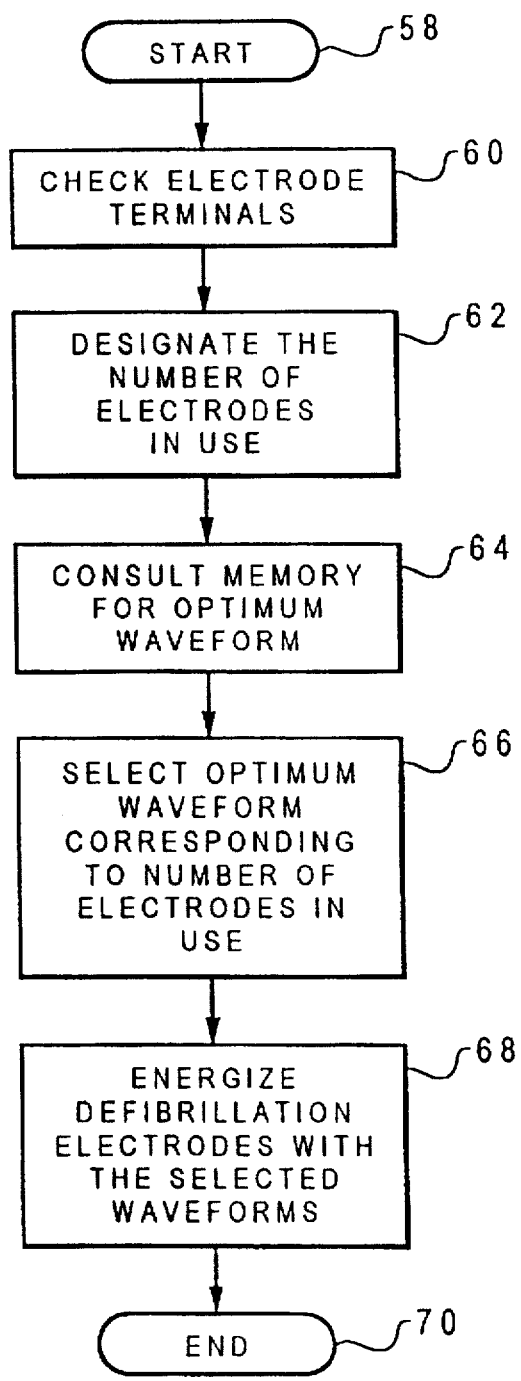
FIG. 4 is a high-level logic flowchart depicting the process whereby the optimum waveform for the number of electrodes in use is selected in accordance with the method and system of the present invention.

Referring now to FIG. 4, which is a high-level logic flowchart depicting the process whereby the optimum waveform for the number of electrodes in use is selected in accordance with the method and system of the invention. Step 58 shows the beginning of the process. Step 60 illustrates the checking of each electrode terminal 16, wherein each connector 14 corresponding to each defibrillation electrode 12 connects to the defibrillation machine 24, for either an open circuit or a closed circuit condition. Step 62 shows the designation of the defibrillation electrodes 12 as in use, dependent upon whether or not there is an open circuit or closed circuit condition detected at each electrode terminal 16, each of which corresponds to a certain defibrillation electrode 12. Step 64 depicts the consultation by the waveform selection circuit 20 of stored memory for the optimum waveform corresponding to the number of electrodes sensed to be in use. Step 66 shows the selection by the waveform selection circuit 20 of this optimized waveform from memory. Step 68 shows the energization of the defibrillation electrodes 12 sensed to be in use, with the waveform optimized to those in-use defibrillation electrodes 12. Method step 70 illustrates the end step of the method wherein the optimum waveform is selected.

While the invention has been particularly shown and described with reference to a preferred embodiment, it will be understood by those skilled in the art that various changes in form and detail may be made therein without departing from the spirit and scope of the invention.

What is claimed is:

1. A method for efficient defibrillation, to be utilized in external defibrillators, capable of being utilized with 2, 3, or more defibrillation electrodes, said method comprising the steps of:

sensing the number of defibrillation electrodes attached to an external defibrillator; and selecting a waveform from among a plurality of waveforms, in response to said number of electrodes sensed, such that said selected waveform is optimized for use with said sensed number of defibrillation electrodes.

2. The method of claim 1, wherein said external defibrillator includes a plurality of electrode terminals and wherein said step of sensing further comprises the steps of:

checking each electrode terminal to detect either an open circuit or a closed circuit condition; and designating a defibrillation electrode corresponding to each of said checked electrode terminals as in use if a closed circuit condition at said checked electrode terminal is detected, or as not in use if an open circuit condition at said checked electrode terminal is detected.

3. The method of claim 1, wherein said selecting step further comprises the steps of:

consulting a stored memory for a series of waveforms optimized for use with said sensed number of defibrillation electrodes; and energizing said sensed number of defibrillation electrodes with said optimal waveform.

4. A device for efficient defibrillation, to be utilized in an external defibrillator having 2, 3, or more defibrillation electrodes, said device having a memory, and said device comprising:

means for sensing the number of defibrillation electrodes attached to an external defibrillator; and means for selecting a waveform from among a plurality of waveforms stored in a memory within said device, in response to said number of electrodes sensed, such that said selected waveform is optimized for use with said sensed number of defibrillation electrodes.

5. The device of claim 4, wherein the external defibrillator further includes a plurality of electrode terminals and wherein said means for sensing further comprises:

means for checking each electrode terminal to detect either an open circuit or a closed circuit condition; and means for designating a defibrillation electrode corresponding to each of said checked electrode terminals as in use if a closed circuit condition at said checked electrode terminal is detected, or as not in use if an open circuit condition at said checked electrode terminal is detected.

6. The device of claim 4, wherein said means for selecting further comprises:

means for consulting a stored memory for a series of waveforms optimized for use with said number of sensed defibrillation electrodes; and means for energizing said sensed number of defibrillation electrodes with said optimal waveform.

* * * * *